United States Patent [19]

Chernin et al.

[11] Patent Number: 4,676,652
[45] Date of Patent: Jun. 30, 1987

[54] MULTIPLE PASS OPTICAL SYSTEM

[76] Inventors: Semen M. Chernin, Vernadskogo, 58, kv. 49, Moscow; Evgenia G. Barskaya, Kirillovskaya, 4, kv. 13; Galina P. Semenova, S. Kovalevskoi, 18, kv. 59, both of Leningrad, all of U.S.S.R.

[21] Appl. No.: 498,200
[22] PCT Filed: Sep. 10, 1981
[86] PCT No.: PCT/SU81/00070
  § 371 Date: May 24, 1983
  § 102(e) Date: May 24, 1983
[87] PCT Pub. No.: WO83/00927
  PCT Pub. Date: Mar. 17, 1983
[51] Int. Cl.[4] ............ G01N 21/01; G02B 5/12; G02B 17/06
[52] U.S. Cl. .................. 356/439; 250/353; 350/619; 356/246
[58] Field of Search ........... 356/445, 244, 246, 446, 356/447, 448, 73, 437, 438, 439; 350/619, 620; 250/353

[56] References Cited

U.S. PATENT DOCUMENTS 3,687,519  8/1972  Mapes .................. 356/73
3,726,598  4/1973  Gilby .................. 356/244
3,963,328  6/1976  Abel ................... 350/619
4,209,232  6/1980  Chernin ............... 356/246
4,210,401  7/1980  Batten ................ 356/244 X

FOREIGN PATENT DOCUMENTS 3014248  10/1981  Fed. Rep. of Germany ...... 356/246
2514515   4/1983  France .
0411356   1/1974  U.S.S.R. .

OTHER PUBLICATIONS

Smith et al., "Method for Obtaining Long Optical Paths", J.O.S.A., Aug., 1940, vol. 30, pp. 338-342.

Primary Examiner—R. A. Rosenberger
Attorney, Agent, or Firm—Lilling & Greenspan

[57] ABSTRACT

A multiple pass optical system comprising a reflecting objective placed across the path of a radiant flux emitted by an illuminator; the objective being mounted pivotally around its own axis. Further, the radiant flux its incident upon a compound collective comprised of two different-curvature mirrors arranged at right angles to each other.

From the lens of the radiant flux, the flux is directed again to the reflecting lens to be reflected therefrom and upon passing the final cycle in the system, it emerges.

4 Claims, 7 Drawing Figures

MULTIPLE PASS OPTICAL SYSTEM

FIELD OF THE INVENTION

The present invention relates to the optical instrument making industry and, more specifically, to multiple pass optical systems.

BACKGROUND OF THE INVENTION

At present multiple pass optical systems featuring a long optical path length are an integral part of every IR spectrophotometer for examination of low-concentration gases or those having very faint absorption bands. Such systems are applicable both for qualitative and quantitative analyses.

One prior-art multiple pass optical system is known (cf. Journal of the Optical Society of America, 1940, v. 30, 338–342, H. D. Smith, L. R. Marshall), wherein the radiant flux emitted by the illuminator passes through the entrance aperture of the casing onto a mirror objective rotatably mounted across the path of the radiant flux, and further onto the unit of intermediate images of the illuminator radiation source, from which the radiant flux is directed again onto the reflecting objective and, on being reflected from said objective, the radiant flux completes the multiple pass cycle and emerges from the system through the exit aperture of the casing. In the above described optical system, the unit of intermediate images of the illuminator radiation source comprises two plane mirrors arranged at an angle to each other.

However, when focusing the intermediate images of the illuminator radiation source in the aforesaid system, the marginal beams fail to get restricted on the flat mirror surfaces, whereby when reflections of the beam are multiply repeated a considerable proportion of the emitted radiant flux is scattered beyond the faces of the reflecting objective (that is, vignetting of the slanted beams occurs).

SUMMARY OF THE INVENTION

The present invention is aimed at the provision of a multiple pass optical system, wherein the unit of the intermediate images of the illuminator radiation source would be so embodied as to increase the luminous transmittance of the system and to simplify the adjustment of the number of passes of the radiant flux.

This is accomplished in a multiple pass optical system, when the radiant flux emitted by the illuminator passes through the entrance aperture of the casing and is incident upon a reflecting objective mounted pivotally about its axis in a path of the radiant flux. The flux is reflected onto the unit of the intermediate images of the illuminator radiation source, from which the radiant flux is directed again onto the mirror objective to be reflected therefrom to complete the multiple-pass cycle by emerging from the system through the exit aperture of the casing thereof, according to the invention, the unit of the intermediate images of the illuminator radiation source is fashioned as a compound collective, comprising two different-curvature mirrors so positioned that the angles of incidence of the radiant flux upon the larger-curvature mirror are less than the angles at which said flux is incident upon the smaller-curvature mirror.

It is expedient that one of the mirrors of the compound collective be planar and the other be concave.

Sometimes it is desirable that both of the mirrors of the compound collective be concave.

It is possible, in order to modify the mode of operation of the multiple pass optical system of the invention, that a holder-carried specimen be placed across the pathway of the radiant flux for the specular reflectance of its plane surface to measure, the mirror objective being so turned round its axis along an arc at the instant the measurement is taken that the radiant flux is alternately incident upon the reflecting objective and the compound collective and upon terminating the final pass of the cycle, the radiation flux is brought directly to the exit aperture.

It is likewise reasonable that the mirror objective be turned round its axis along an arc by means of a pivotally mounted lever arranged coaxially with the specimen holder and carrying the reflecting objective at one of its ends.

The present invention makes it possible to avoid vignetting of the slanted beams in the radiant flux whatever the number of its passes within the optical system. This in turn improves the luminous transmittance of the system and renders the latter less dependent upon the number of radiant flux passes.

Furthermore, the present invention makes the adjustment of the number of the radiant flux passes more simple as the system can be adjusted for a preset number of passes more precisely.

In addition, the present invention is instrumental in attaining more precise measurements of the specular reflectance of small-sized plane specimens.

BRIEF DESCRIPTION OF THE DRAWINGS

In what follows the present invention will now be disclosed in a detailed description of specific illustrative embodiments thereof to be had in conjunction with the accompanying drawings. In the drawings:

FIG. 5 is a side, elevational view, partly in section, of a structural diagram of a multiple pass optical system.

DETAILED DESCRIPTION OF THE INVENTION

To exemplify the present invention a multiple pass optical system will hereinafter be considered in detail when the radiant flux performs six passes within said optical system.

Figure 1:
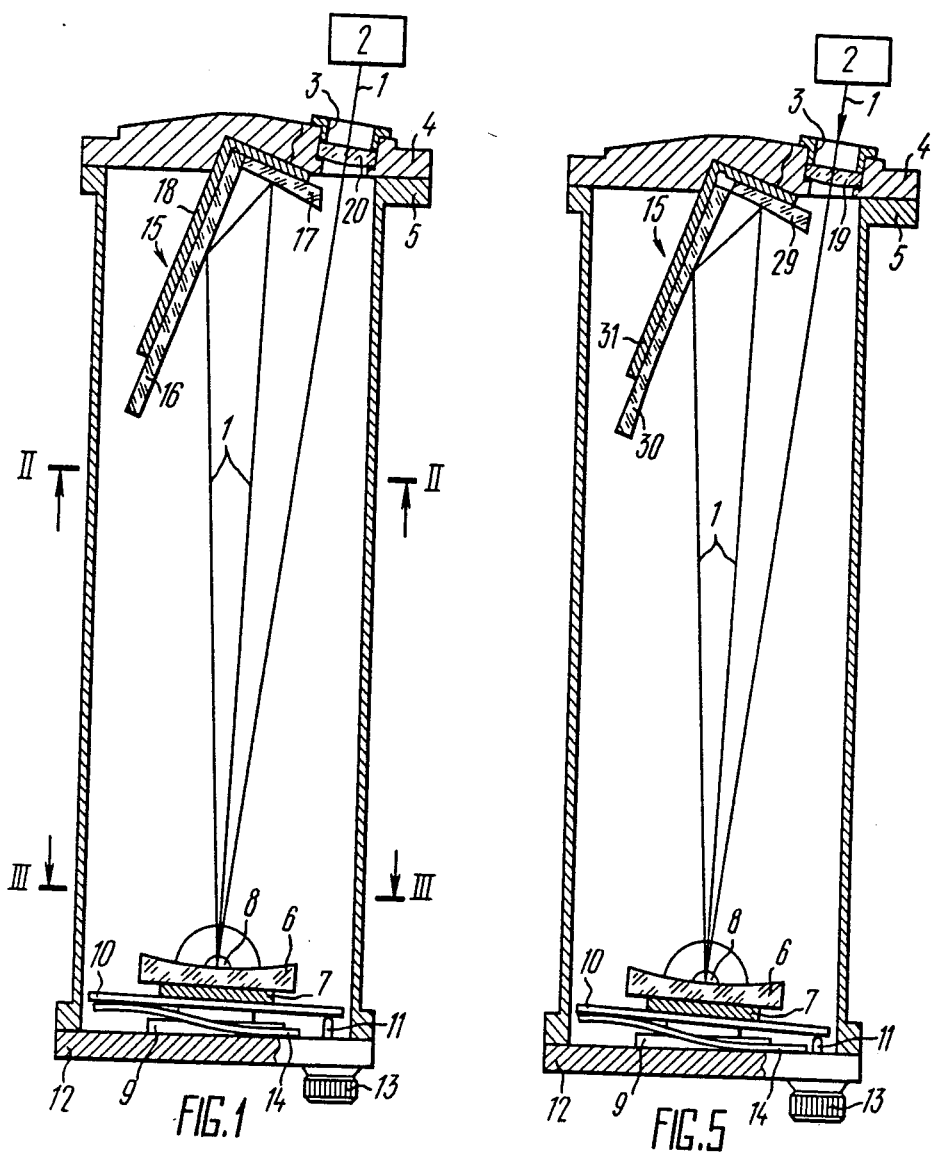
FIG. 1 is a side, elevational view, partly in section, of a multiple pass optical system having a sextuple passing of the radiant flux.
Figure 2:
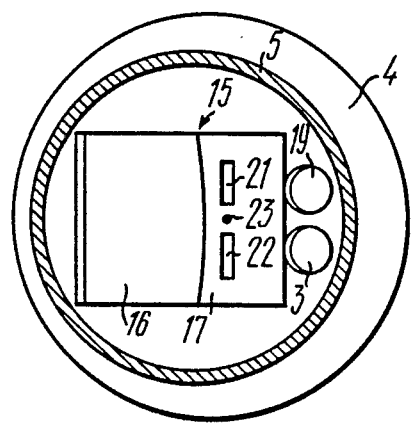
FIG. 2 is a cross-sectional view taken along line II—II in FIG. 1.
Figure 3:
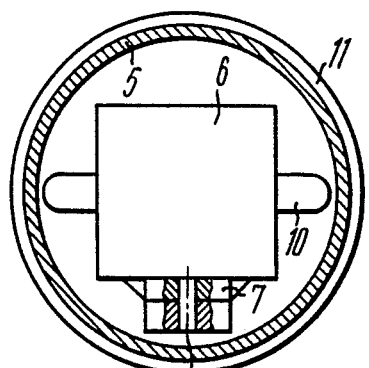
FIG. 3 is a cross-sectional view taken along lines III—III in FIG. 1.

Referring to the accompanying drawings, FIG. 1 represents the multiple pass optical system, wherein a radiant flux 1 emitted by an illuminator 2 passes through an entrance aperture 3 (FIGS. 1, 2) provided in a lid 4 of a casing 5 and is incident upon a mirror objective 6 (FIGS. 1, 3).

The objective 6 is placed across the path of the radiant flux 1 and fixed in a holder 7, which is mounted on a bracket 9 pivotally about an axle 8. Fastened on the holder 7 is a strip 10 against which thrusts a screw 11 adapted to adjust the number of passes of the radiant flux 1, said screw extending through a cover 12 of the casing 5. The adjustment is carried out by rotating a knob 13 coupled to the screw 11. The strip 10 is locked in position by a flat spring 14 made fast on the cover 12.

A compound collective 15 (FIGS. 1, 2) is placed across the path of the radiant flux 1 reflected from the objective 6, said compound collective comprising two different-curvature mirrors, of which one is a plane mirror 16 and the other, a concave mirror 17. The mirrors 16 and 17 are so positioned that the angles of incident of the radiant flux 1 upon the concave mirror 17 are less than the angles of incident of said flux upon the plane mirror 16. Both of the mirrors 16 and 17 are mounted in a holder 18 fixed on the lid 4. An exit aperture 19 is made in the lid 4 above the entrance aperture 3, through which the radiant flux 1 emerges from the optical system upon performing the final pass therein. Windows 20 are fitted in the apertures 3 and 19 transparent for the given luminous flux 1.

The objective 6 forms on the surface of the mirror 17 two intermediate images 21 and 22 of the radiation source (not shown) of the illuminator 2, said images being arranged symmetrically with respect to a centre 23 of curvature of the objective 6.

Figure 4:
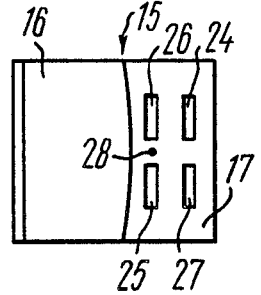
FIG. 4 is a top view of a compound collective of the optical system.

In the case of a tenfold passing of the radiant flux 1 the reflecting objective 6 forms four intermediate images 24, 25, 26, 27 of the radiation source of the illuminator 2 on the mirror 17 of the compound collective 15 (FIGS. 1, 4). A centre 28 of curvature of the objective 6 is located between the images 25 and 26.

According to another embodiment of the invention of a multiple pass optical system the compound collective 15 (FIG. 5) comprises two different-curvature concave mirrors 29 and 30 mounted in a holder 31, which is fixed in the lid 4. The mirrors 29 and 30 are so positioned with respect to the radiant flux 1 that the angles of incident of the radiant flux 1 upon mirror 29 having a greater curvature are less than the angles of incident of the radiant flux 1 upon the mirror 30.

Figure 6:
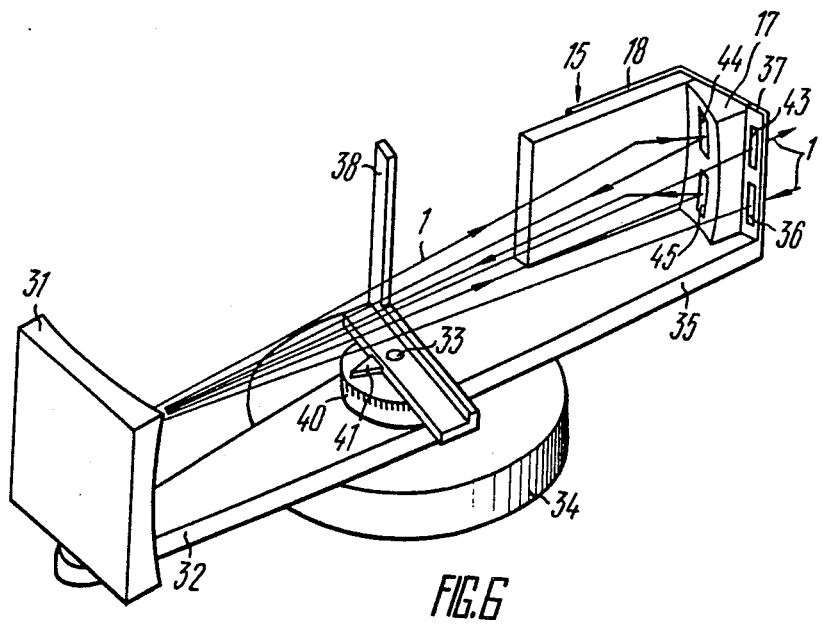
FIG. 6 is a perspective view of a multiple pass optical system operating as a reflectometer at the instant of adjustment.
Figure 7:
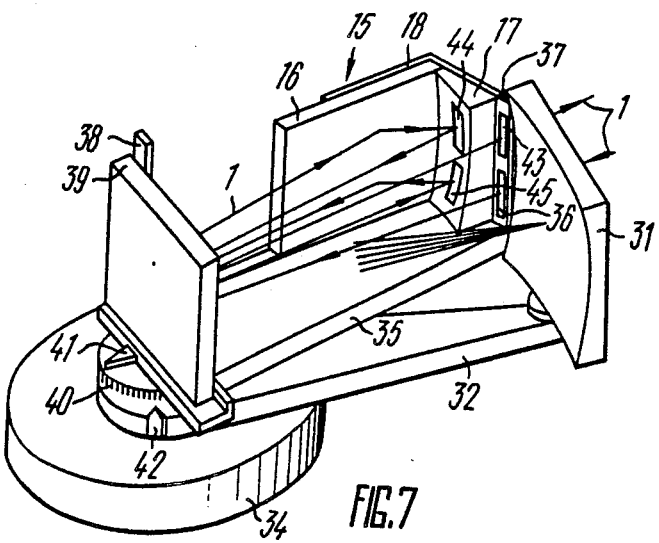
FIG. 7 is a perspective view of a multiple pass optical system operating as a reflectometer illustrating the measurements of the specular reflectance of the specimen plane surface.

In another embodiment of a multiple pass optical system involving sextuple passing of the radiant flux 1 (FIGS. 6, 7) and operating as a reflectometer, the mirror objective 31 is movably mounted at one end of an arm 32, while its other end is fitted onto a central pivot axle 33, which is dead-locked in a base 34. The holder 18 of the compound collective 15 is located on a bed 35, which is stationary fixed on the pivot axle 33 above the arm 32. A swivel holder 38 is placed across the pathway of the radiant flux 1 passing through an orifice 36 of a diaphragm 37 (its case being not shown), said holder being mounted on the pivot axle 33 and carrying a specimen 39 (FIG. 7) for the specular reflectance of its plane surface (not shown) to measure. The diaphragm 37 (FIGS. 6, 7) is situated on the bed 35.

The bed 35 is provided with an arc scale 40 graduated in angular measures, while the holder 38 and the arm 32 have respective fixed indexes 41 and 42 to read said graduations of the scale 40. When setting the specimen 39 (FIG. 7) in the holder 38 the objective 31 is so turned along an arc by means of the arm 32 that the radiant flux 1, after having been reflected from the specimen 31 and the compound collective 15 and upon performing the final pass it is directed to an exit orifice 43 (FIGS. 6, 7) of the diaphragm 37. The concave mirror 17 shows intermediate images 44 and 45 of the radiation source of the illuminator 2 (FIG. 1).

The multiple pass optical system, adjusted for a sextuple passing of the radiant flux and used for spectrophotometric examinations of gases, operates as follows.

The casing 5 (FIG. 1) of the system is filled with the gas under examination. The radiant flux 1 emitted by the illuminator 2 passes through the window 20 of the entrance aperture 3 and is incident upon the mirror objective 6, which forms the intermediate image 21 (FIG. 2) of the radiation source of the illuminator 2 (FIG. 1) on the top portion of the concave mirror 17 of the compound collective 15 upon its having been reflected from the plane mirror 16 thereof. Having been reflected from the mirrors 16 and 17 the divergent radiant flux 1 is directed again to the objective 16 to be reflected therefrom, and is then focused on the bottom portion of the concave mirror 17 as the intermediate image 22 (FIG. 2) of the radiation source of the illuminator 2 (FIG. 1). Subsequently the radiant flux 1, having been reflected from the plane mirror 16, is reflected onto the objective 6 to be reflected therefrom and finally pass to the exit aperture 19 to emerge from the optical system.

In cases where use is made of the compound collective 15 made up of the two concave mirrors 29 and 30, it is possible to compensate for some aberration distortions of the images of the illuminator 2 radiation source. The optical system operates in a way similar to that described above.

According to the invention, the compound commective 15 provides for multiple optical conjugation of the mirror objective 6 with itself, thereby eliminating the phenomenon of vignetting in the system.

When shifting the centre 28 (FIG. 4) of the curvature of the objective 6 (FIG. 1) due to the latter being turned towards the joint between the mirrors 16 and 17 of the compound collective 15, the number of passes of the system is increased. In the case of tenfold passing of the flux 1, the images 24, 25, 26 and 27 of the radiation source of the illuminator 2 (FIG. 1) are consecutively formed.

When operating as a reflectometer the multipass optical system involving sextuple passing of the radiant flux operates with two different positions of the mirror objective 31 (FIGS. 6, 7) with respect to the compound collective 15, corresponding to taking measurement with the specimen 39 (FIG. 7) or without it.

With the objective 31 (FIG. 6) in the initial position without a specimen, the reflectometer operates in a way similar to that described above, a signal I of the radiant flux 1 being picked off the exit aperture 43 of the system.

Then the specimen 39 (FIG. 7) is fitted in the holder 38 for the specular reflectance of its plane surface to measure, while the mirror objective 31 is moved by the arm 32 along an arc round the central pivot axle 33 so that the radiant flux reflected from the specimen 39 is incident upon the reflecting objective 31. The positions of the objective 31 and specimen 39 are indicated by the indexes 41 and 42 on the scale 4 graduated in angular measures, located on the bed 35. The flux 1 reflected from the mirror objective 31 is directed again to the specimen 39 to be reflected therefrom and directed to the compound collective 15, whereupon the intermediate images 44 and 45 of illuminator radiation source are formed. Thus, when performing each pass through the multiple pass optical system, the radiant flux 1 is reflected from the specimen 39, whereas the other elements of the optical system function in the same way. Intensity $I_1$ of the signal I, when measuring the transmittance value at the exit of the system with a specimen will decrease in proportion with specimen reflectance R in a degree equal to the number K of the passes performed by the radiant flux. The reflectance R of the specimen 39 is found from the relation $$R = \sqrt[K]{\frac{I_1}{I}} \ .$$

INDUSTRIAL APPLICABILITY

The present invention can find most successful application when used for increasing the instrumental sensitivity of measurement in IR absorption spectrophotometry.

The invention is also applicable in quick-acting high-precision optoacoustical gas analyzers without the use of spectrometrical equipment, in particular, for quantitative determination of the atmospheric pollution, which is of importance in connection with environmental protection.

In addition, the present invention can be applied for high-precision measurement of the reflectance of plane specimens at low angular divergence of light beams, which is of great interest for laser technology and high-energy plants.

We claim:

1. An improved multiple pass optical system having a radiation source illuminator located outside a first end of a casing and passing a radiant flux through an entrance aperture of said casing into a mirror objective placed around a path of the radiant flux, and pivotally mounted about its axis near a second end of said casing, said radiant flux reflected from said mirror objective onto a unit having immediate images and directed again onto said mirror objective and performing a final pass through said system prior to emerging through an exit aperture of said casing adjacent to said entrance aperature, wherein the improvement of said system comprises said unit having immediate images having a compound collective located adjacent to the first end of said casing in said path of said radiant flux between the illuminator and the mirror objective, and having a first mirror in a first position in the path of the radiant flux of a greater curvature and reflecting lesser angles of incidence of said flux in comparison to a second mirror in a second position in the path of said radiant flux of a lesser curvature and reflecting greater angles of incidence of said radiant flux.

2. A multiple pass optical system according to claim 1, wherein said first mirror of said compound collective is concave and said second mirror is planar.

3. A system according to claim 1, wherein said first and second mirrors of said compound collective are concave.

4. A system according to claim 1, wherein a holder holding a specimen is mounted in said path of said radiant flux between said compound collective and said mirror objective to one end of an arm, and said mirror objective is mounted to a second end of said arm in a pivotal and coaxial relation to said holder, said arm rotating about its said first end moving the mirror objective in an arcuate direction about said holder resulting in the alternation of the angles of incidence of the radiant flux upon said mirror objective and said compound collective to measure a specular reflectance of a plane surface of said specimen.

* * * * *